United States Patent [19]

Upsher

[11] Patent Number: 4,546,762

[45] Date of Patent: Oct. 15, 1985

[54] LARYNGOSCOPE INCLUDING A LATERALLY OFFSET BLADE

[76] Inventor: Michael S. Upsher, 2957 Adeline Dr., Burlingame, Calif. 94010

[21] Appl. No.: 501,538

[22] Filed: Jun. 6, 1983

[51] Int. Cl.⁴ ............................................. A61B 17/24
[52] U.S. Cl. ..................................................... 128/11
[58] Field of Search .................................. 128/10, 11

[56] References Cited

U.S. PATENT DOCUMENTS

| | | | |
|---|---|---|---|
| 2,354,471 | 7/1944 | MacIntosh | 128/10 |
| 3,766,909 | 10/1973 | Ozbey | 128/11 |
| 4,037,588 | 7/1977 | Heckele | 128/11 |
| 4,086,919 | 5/1978 | Bullard | 128/11 |
| 4,314,551 | 2/1982 | Kadell | 128/11 |

FOREIGN PATENT DOCUMENTS

| | | | |
|---|---|---|---|
| 1278067 | 9/1968 | Fed. Rep. of Germany | 128/10 |
| 2738202 | 3/1979 | Fed. Rep. of Germany | 128/11 |

*Primary Examiner*—Kyle L. Howell
*Assistant Examiner*—Ruth S. Smith
*Attorney, Agent, or Firm*—Flehr, Hohbach, Test, Albritton & Herbert

[57] ABSTRACT

A laryngoscope comprising a handle and a blade disengagably connected therewith is disclosed therein. The handle includes an elongated, straight hand gripping segment containing a power source. The blade includes a handle connecting backend segment containing a light source and an elongated tongue lifting and tube guiding front segment which carries a light guide. This latter segment is made up of first and second subsegments extending its entire length, the first subsegment being disposed within a plane through the elongation axis of the hand gripping segment and serving to contain a light guide and the second subsegment being disposed laterally to one side of the same plane and serving to elevate the patient's tongue and to guide an endotracheal tube into the patient's throat.

3 Claims, 6 Drawing Figures

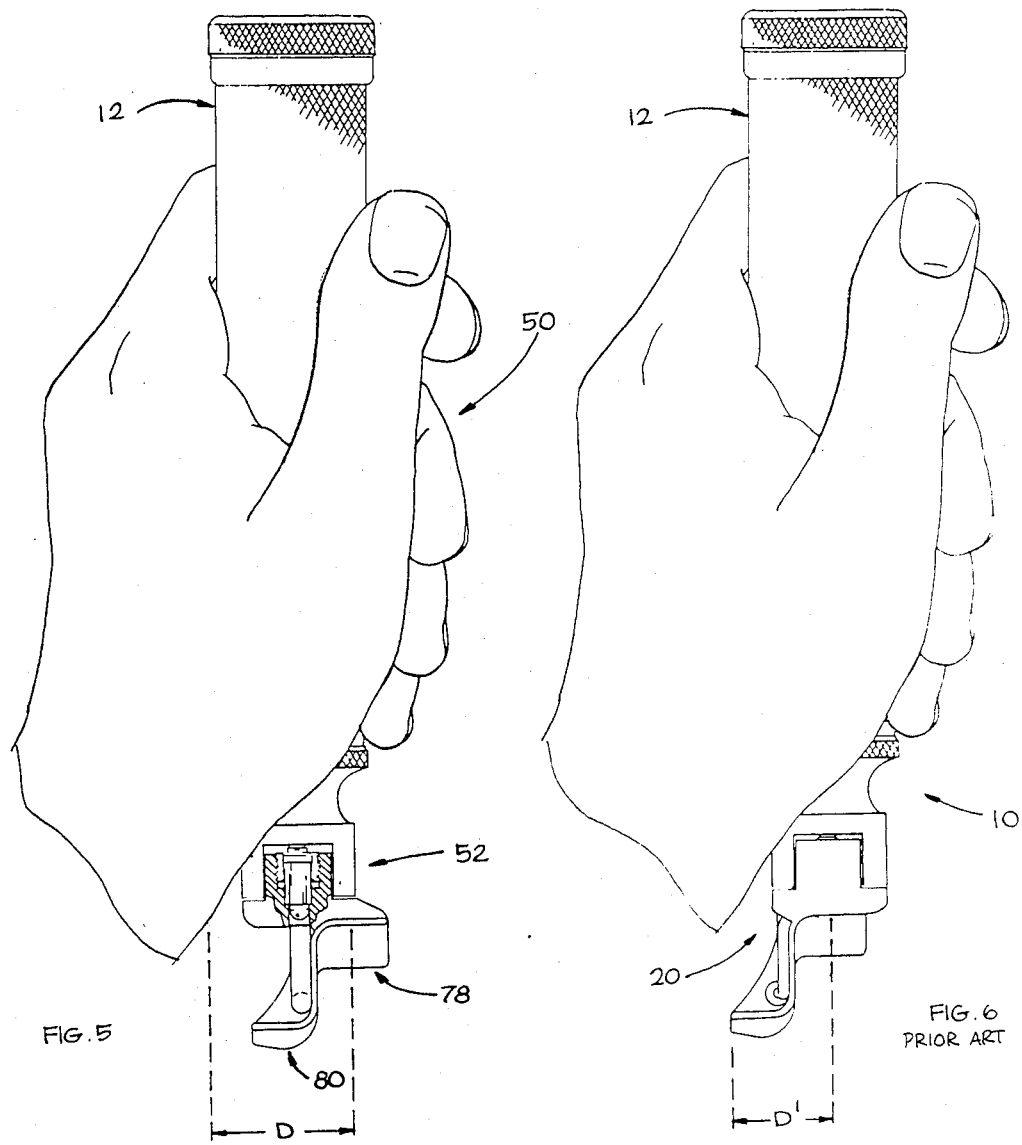

LARYNGOSCOPE INCLUDING A LATERALLY OFFSET BLADE

The present invention relates generally to a laryngoscope and more particularly to a laryngoscope comprised of a conventional or standard handle and a specifically designed non-standard blade engagably connectable with the handle in a laterally offset operating position.

As used herein, the "standard laryngoscope" refers to the one specifically illustrated in FIGS. 1 and 2, generally designated by the reference numeral 10. This laryngoscope includes a handle 12 having an elongated, straight hand gripping segment 14, and a blade connecting head segment 16 extending up from the uppermost end 18 (FIG. 2) of segment 14. This laryngoscope also includes a blade 20 separate from the handle and having a handle connecting back segment 22 and an elongated, slightly curved tongue lifting and endotracheal tube guiding front segment 24 extending out from segment 22. As seen best in FIG. 2, segment 16 includes a pair of spaced apart support flanges 26 extending up from the uppermost end 18 of hand gripping segment 14. A blade supporting pin 28 (FIG. 1) is connected to and between these flanges near the front, top end of the latter. The handle connecting back segment 22 of blade 20 includes a front jaw-shaped section 30 defining a slot 32 (FIG. 1) and a rearward base 34 (FIG. 2). Blade 20 is disengagably connected to handle 12 by engaging the slot 32 around support pin 28 and thereafter rotating base 34 into its FIG. 2 position between flanges 26. While not shown in FIGS. 1 or 2, the flanges 26 and base 34 include cooperating means for maintaining blade in its operating position.

In addition to the components thus far described, standard laryngoscope 10 includes a power supply, e.g. one or more batteries (not shown), contained within hand gripping segment 14 of handle 12 and an electrical contact 35 located at the uppermost end of and carried by segment 14 along the elongation axis 46 of the latter. At the same time, blade 20 carries its own light source 36, e.g. a light bulb, at the front end of the segment 24 and a contact 38 electrically connected to the light source by means of a conduit contained lead wire 40. Contact 38 is carried by base 34 on the underside of the latter in a position so as to engage contact 35 when the blade is placed in its operating position. This closes an electrical circuit between the power supply in handle 12 and the light source so as to cause the latter to energize.

As best illustrated in FIG. 2, the tongue 24 of blade 20 may be separated into laterally adjacent subsegments 42 and 44 extending its entire length. Subsegment 42 is located in a plane extending through the elongation axis 46 of hand gripping segment 14 and serves to lift the patient's tongue and guide an endotracheal tube into the throat of a patient. Subsegment 44 which is disposed laterally to one side of subsegment 42 serves to contain lead wire 40. This positional relationship between the subsegments 42 and 44 and the rest of the laryngoscope has certain drawbacks. First, it should be noted that subsegment 42 is what may be considered the working subsegment of the blade in that it is used to physically guide the endotracheal tube into the patient's throat, as stated. Since this subsegment is in direct line with the handle's hand gripping segment, it is located relatively close to the user's hand, actually his wrist when properly gripped, as best illustrated in FIG. 6. This makes it more difficult for the user to manipulate the endotracheal tube along the guiding surface of subsegment 42. Another disadvantage of this positional relationship resides in the desire to replace the light source 36 at the front end of blade 20 with a light guide and relocate the light source in base 34 directly over contact 38, as will be seen hereinafter. With the particular positional relationship between subsegments 42 and 44 and base 34, this requires that the light guide be bent a number of times. Specifically, in order for the rearwardmost end of the light guide to be placed in optical communication with a relocated light source, it would have to be bent downward (FIG. 1) and thereafter to the left and then again downward, (see the dotted lines in FIG. 2).

In view of the foregoing, it is one object of the present invention to provide a laryngoscope including a handle and a blade which is disengagably connectable with the handle in a laterally offset manner so as to place its working surface (e.g., its endotracheal tube guiding surface) further from the user's grip when the laryngoscope is held in a normal operating position.

Another object of the present invention is to provide the last-mentioned laryngoscope with a standard laryngoscope handle.

Still another object of the present invention is to provide the last-mentioned laterally offset blade with a light source at its rearward handle connecting end and a light guide extended therefrom to the front end of the blade, all of which, except for a forwardmost end section of the light guide, are disposed in a common plane extending through the elongation axis of the handle when the blade is in its operating position on the handle.

As will be seen hereinafter, the overall laryngoscope disclosed herein includes a standard handle of the type described above, specifically one which includes an elongated, straight hand gripping segment containing a battery or batteries and a blade connecting head segment extending up from the uppermost end of the hand gripping segment as well as the previously described electrical contact 35 located on the axis of the hand gripping segment. The laryngoscope also includes a separable blade having a handle connecting back segment and a tube guiding front segment as well as first and second cooperating means respectively forming parts of the head segment of the handle and the handle connecting segment of the blade for disengagably connecting the blade in an operating position to the handle.

In accordance with one aspect of the present invention, the handle connecting segment of the blade carries means including a light source and its own electrically connected contact in a location which places this latter contact and the light source over and directly adjacent contact 35 such that the contacts engage one another and thereby energize the light source. A light guide is carried by the tube guiding segment of the blade and has a rearwardmost end in optical alignment with the light source and forwardmost end section. This light guide, with the exception of its forwardmost end section, is disposed within a single plane which extends through the elongation axis of the handle's hand gripping segment when the blade is in its operating position and therefore it is not required to be bent outside of this plane.

In accordance with another aspect of the present invention, the tongue of the blade just recited includes laterally adjacent first and second subsegments extending its entire length. The first of these subsegments is disposed within the plane of and serves to contain the light guide. The second subsegment, which serves to lift the patient's tongue and guide an endotracheal tube into his throat, is located to one side of the first subsegment and laterally offset with respect to the elongation axis of the handle further from the wrist of the user when the laryngoscope is held in its operating position.

Both of the aspects of the present inention just recited will be discussed in more detail hereinafter in conjunction with the drawings wherein:

FIG. 5 is an enlarged back elevational view of the laryngoscope of FIGS. 3 and 4 shown in its entirety in its operating position while being gripped by the user; and FIG. 6 is a view similar to the FIG. 5 but showing the standard laryngoscope shown in FIGS. 1 and 2 in the grips of the user.

Figures 1, 2, 3, 4:
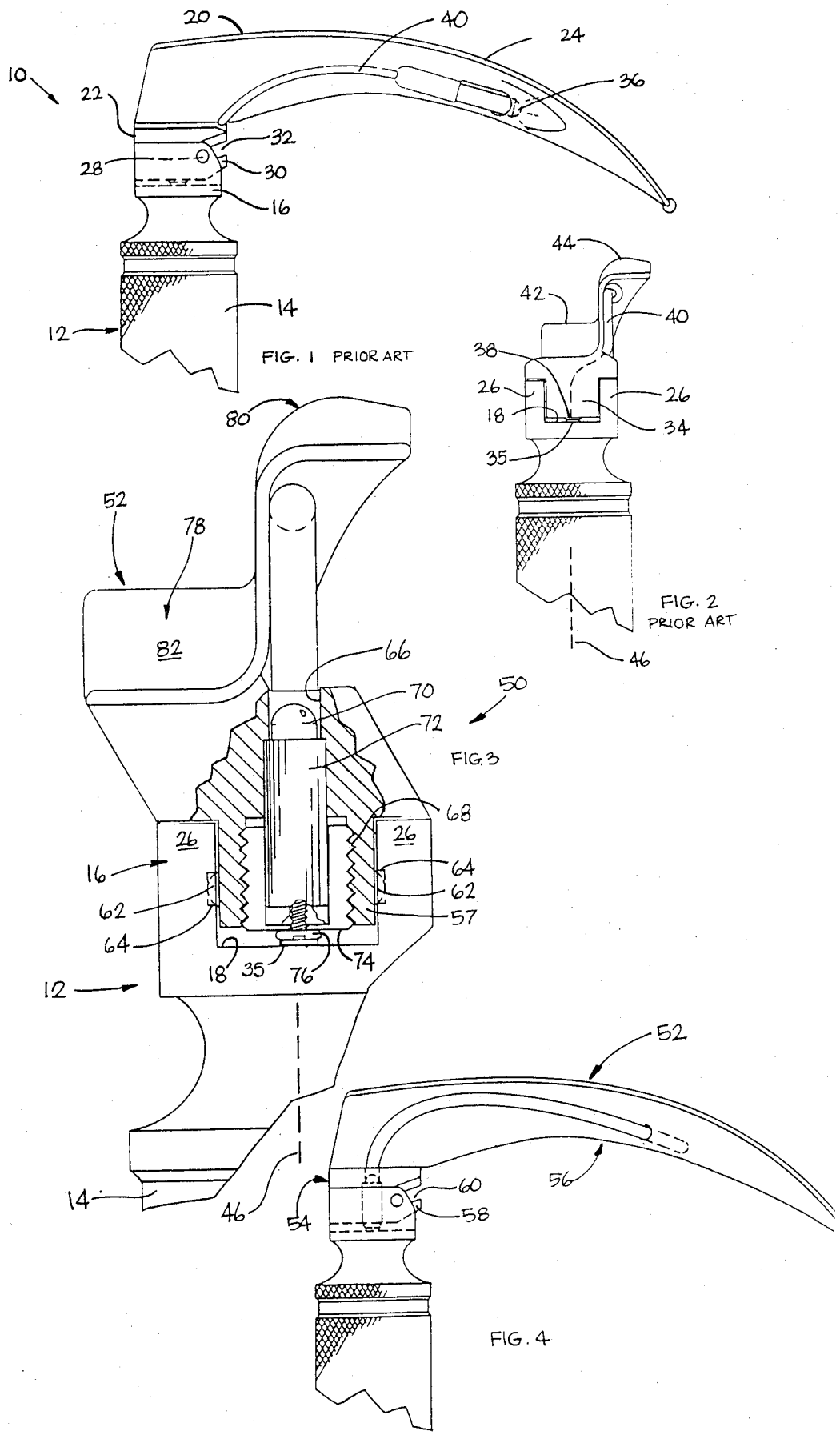
FIGS. 1 and 2 are side and back elevational views, respectively, of a "standard" laryngoscope including a standard handle and a standard blade, as described above.
FIG. 3 is an enlarged front elevational view of a laryngoscope including a laterally offset laryngoscope blade designed in accordance with the present invention for use with the standard handle shown in FIGS. 1 and 2, the laterally offset blade being illustrated in a disengagably connected operating position on the standard handle.
FIG. 4 is a side elevational view of the blade and a handle shown in FIG. 3.

Turning now to the drawings wherein like components are designated by like reference numerals, attention is immediately directed to FIGS. 3 and 4, inasmuch as the standard laryngoscope shown in FIGS. 1 and 2 was described above. FIGS. 3 and 4 illustrate an overall laryngoscope 50 which is comprised of previously described standard handle 12 and a laterally offset laryngoscope blade 52 designed in accordance with the present invention. As described above, standard handle 12 includes a elongated, straight gripping segment 14 defining elongation axis 46 (FIG. 2) and a blade connecting head segment 16 comprised of spaced-apart flanges 26 and support pin 28 (See FIG. 1). The handle also includes battery or batteries contained within its hand gripping segment 14 and electrically connected contact 34 located along elongated axis 46 in surface 18 of the hand gripping segment.

With specific reference to FIGS. 3 and 4, attention is now directed to various features of laryngoscope blade 52. As shown there, this blade includes its own handle connecting back segment 54 and tongue front segment 56 extending out from segment 54. Like previously described segment 22 of blade 20, segment 54 includes a base 57 adapted to fit over handle surface 18 between flanges 26 and a jaw portion 58 defining slot 60 configured to receive support pin 28. Segment 54 disengagably connects to handle 12 in the same manner as segment 22 of blade 20. In otherwords, segment 54 of the blade and segment 12 of the handle together form first and second cooperating means for disengagably connecting the blade to the handle. Moreover, in order to maintain blade 52 in its operating position illustrated in FIGS. 3 and 4, base 57 includes a pair of dimples 62 extending outwardly on opposite sides of the base. These dimples are designed to fit within cooperating indents in flanges 26, as illustrated in FIG. 3.

In accordance with one feature of the present invention, base 57 of blade 52 includes a vertically extending, open-ended passageway 66 which is counterbored and threaded along a lowermost end section to provide a larger, threaded opening 68. This combination passageway is designed to receive a light bulb 70 within its own casing 72. The light bulb and casing fit within an externally threaded insert 74 which is configured to thread within passage 68, as illustrated in FIG. 3. The bottom end of casing 72 carries a contact 76 which is electrically connected to the positive side of the light source. The negative side of the light source (ground) is electrically connected to the blade body which is ultimately grounded to the handle when the blade is in its operating position. With the blade in this latter position, contact 76 engages previously described contact 35. This automatically places the light source in electrical circuit with the batteries which therefore causes the batteries to automatically energize the light source.

As stated previously, the tongue of the standard laryngoscope blade 20 includes laterally adjacent subsegments 42 and 44. Tongue 56 of blade 52 includes similar subsegments 78 and 80. Subsegment 78 serves as a means of elevating the patient's tongue and a guide for an endotracheal tube and may be identical structurally to subsegment 42 except for its position relative to the handle 12. Specifically, subsegment 78 extends from the back end of segment 56 to its forwardmost end so as to define a curved endotracheal tube guiding surface 82. Subsegment 80 structurally corresponds to subsegment 44, again except for its position relative to handle 12. Also, subsegment 80 does not support its previously recited light source 36 and associated lead wire 40, but rather a light guide 84 having a forwardmost end section 85. As best illustrated in FIG. 4, this light guide is bonded, embedded or otherwise fixedly connected to subsegment 80 and its forwardmost end section 85 is disposed near the forwardmost tip of the subsegment. Its back end is disposed in optical alignment with light bulb 70 as best seen in FIG. 3. In this latter regard, it is to be noted that the entire subsegment 80 and the entire light guide, except for section 85, is disposed in a common place with the light bulb and its casing and therefore in a common plane with elongation axis 46 when the blade 50 is in its operating position on handle 12. This is to be contrasted with corresponding subsegment 44 which is located to one side of base 34 and therefore offset laterally relative to axis 46, as best seen in FIG. 2. While not exactly shown in FIG. 4, forwardmost end section 85 of light guide 84 bends inward (into the paper) so as to direct light from the light source in the proper direction.

As just stated, subsegment 80 of laryngoscope blade 50 is located directly over base 57 and light bulb 70. At the same time, endotracheal tube guiding subsegment 78 is laterally offset to one side of said subsegment 80 and therefore it is laterally offset to one side of elongation axis 46. This is to be contrasted with corresponding subsegment 42 which, as shown in FIG. 2, is located in a common plane with elongation axis 46. This contrast is best illustrated in FIGS. 5 and 6. FIG. 5 shows laryngoscope blade 52 on handle 12 which is held in its operating position. FIG. 6 is a similar view of blade 20 on handle 12. Note that the tube guiding subsegment 78 of blade 52 is located laterally further from the user's wrist than the subsegment 42 by an amount equal to the difference of D−D′ where these two dimensions represent the distances from the same point on the user's wrist. By laterally offsetting subsegment 78, the user can more readily guide an endotracheal tube in place with his right hand as he holds the handle in his left hand (the standard holding technique). Moreover, by doing this, most of the light guide 84, light source 70 and contact 76 can all be placed in planar alignment with contact 34, thereby making the overall construction relatively simple and minimizing the number of bends which are required in the light guide itself.

What is claimed is:

1. A laryngoscope, comprising:
   (a) a handle including an elongated, straight hand gripping segment defining an elongation axis and having an uppermost end and a blade connecting head segment extending up from said uppermost end;
   (b) a blade disengagably connected to said handle and including a handle connecting back segment and an elongated front segment extending out from said handle connecting segment, said front segment being divided into first and second laterally adjacent subsegments extending its entire length, said first subsegment serving a means for lifting a patient's tongue and having a surface for guiding an endotracheal tube into the patient's throat, said second subsegment extending up from said tube guiding surface for containing a light guide;
   (c) first and second cooperating means respectively forming parts of the blade connecting head segment of said handle and the handle connecting back segment of said blade for disengageably connecting said blade in an operating position to said handle such that the back segment of the blade is directly over the uppermost end of the handle's hand gripping segment and such that said second subsegment of the blade's front segment is within a single plane extending through the elongation axis of the handle's hand gripping segment;
   (d) means including a light source and electrically connected first contact means carried by the handle connecting back segment of said blade in a location which places said contact means and light source over and directly adjacent the uppermost end of the handle's hand gripping segment along said elongation axis of the latter when said blade is in said operating position;
   (e) a light guide carried by the second subsegment of the front segment of said blade and having a rearwardmost end in optical alignment with said light source and a forwardmost end section closer to the forwardmost end of the blade; and
   (f) means including a power source carried by the hand gripping segment of said handle and electrically connected second contact means located at the uppermost end of the handle's hand gripping segment on the elongation axis of the latter, said means including said power source cooperating with said means including said light source so as to cause said second contact means to engage said first contact means when said blade is in said operating position and energize said light source, whereby to cause light therefrom to pass through said light guide.

2. A laryngoscope blade for use with a standard laryngoscope handle said blade comprising:
   (a) a blade body including back segment connecting means adapted to connect said blade to a handle and an elongated front segment extending out from said connecting means, said front segment being divided into first and second laterally adjacent subsegments extending its entire length, said first subsegment being located to one side of a plane extending through said connecting means and serving as means for lifting a patient's tongue and having a surface for guiding an endotracheal tube into the patient's throat, said second subsegment extending up from said tube guiding surface entirely within said plane and containing a light guide.

3. A laryngoscope, comprising:
   (a) a handle including an elongated, straight hand gripping segment defining an elongation axis and having an uppermost end and a blade connecting head segment extending up from said uppermost end; and
   (b) a blade disengagably connected to said handle and including a handle connecting back segment and an elongated front segment extending out from said handle connecting segment, said front segment including laterally adjacent first and second subsegments extending its entire length, said second subsegment being disposed within a single plane extending through the elongation axis of the handle's hand gripping segment and containing a light source associated conduit, said first subsegment being disposed laterally to one side of said plane and serving to elevate the patient's tongue and guide an endotracheal tube into the patient's throat.

* * * * *